United States Patent
Subelka et al.

(10) Patent No.: US 6,696,507 B2
(45) Date of Patent: Feb. 24, 2004

(54) DENTAL COMPOSITE RESTORATIVE MATERIAL AND METHOD OF RESTORING A TOOTH

(75) Inventors: John C. Subelka, Marlboro, NJ (US); Steven R. Jefferies, York, PA (US); Donald A. Kapperman, Milford, DE (US); Paul D. Hammesfahr, Wyoming, DE (US); Paul A. Silver, Wilmington, DE (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 10/036,881

(22) Filed: Jan. 4, 2002

(65) Prior Publication Data

US 2003/0060532 A1 Mar. 27, 2003

Related U.S. Application Data

(62) Division of application No. 09/136,320, filed on Jul. 6, 1998, now Pat. No. 6,353,040, which is a continuation of application No. 09/052,180, filed on Mar. 31, 1998, now abandoned, which is a continuation of application No. 08/946,612, filed on Oct. 7, 1997, now abandoned.
(60) Provisional application No. 60/043,812, filed on Apr. 14, 1997, and provisional application No. 60/042,585, filed on Apr. 2, 1997.

(51) Int. Cl.[7] .............................. A61C 5/00; A61K 6/08; C08K 3/34
(52) U.S. Cl. ................... 523/115; 523/116; 523/117; 523/118; 523/119; 523/120; 524/493; 524/494; 433/228.1; 428/35.7
(58) Field of Search ................. 523/115, 116, 523/117, 118, 119, 120; 524/493, 494; 433/228.1; 428/35.7

(56) References Cited

U.S. PATENT DOCUMENTS

| 4,107,845 A | 8/1978 | Lee, Jr. et al. ................... 32/15 |
| 4,115,346 A | 9/1978 | Gross et al. ............. 260/42.15 |
| 4,141,144 A | 2/1979 | Lustgarten ...................... 32/15 |
| 4,226,622 A | 10/1980 | Aliotta et al. ................. 75/251 |
| 4,350,532 A | 9/1982 | Randklev ..................... 106/30 |

(List continued on next page.)

FOREIGN PATENT DOCUMENTS

| DE | 34 16 083 | 10/1985 |
| DE | 195 24 362 | 1/1996 |
| EP | 0053442 | 6/1982 |
| EP | 475239 | 9/1991 |
| EP | 0222899 | 4/1992 |

(List continued on next page.)

OTHER PUBLICATIONS

Aerosil R972. Datasheet by DeGussa. 1994.*

Primary Examiner—Tae H. Yoon
(74) Attorney, Agent, or Firm—Douglas J. Hura; James B. Bieber (57) ABSTRACT

A dental composite material includes a hardenable resin matrix and a filler component. The filler component includes (a) a first plurality of preferably glass particles having an average particle size of from about 1 to about 10 micrometers; (b) a second plurality of preferably glass particles having an average particle size of from about 0.1 to about 1 micrometers; and, (c) a plurality of filler particles having an average particle size of from about 0.01 to about 0.04 micrometers. A method according to the invention includes compacting a dental composite material into a prepared tooth cavity, wherein the material has a packability index above about 300 g/mm$^2$.

2 Claims, 3 Drawing Sheets

U.S. PATENT DOCUMENTS

| | | | | |
|---|---|---|---|---|
| 4,358,549 | A | 11/1982 | Randklev | 523/117 |
| 4,360,693 | A | 11/1982 | Orlowski | 560/220 |
| 4,375,967 | A | 3/1983 | Schaefer | 433/199 |
| 4,379,695 | A | 4/1983 | Orlowski | 433/217 |
| 4,381,918 | A | 5/1983 | Ehrnford | 43/199 |
| 4,387,240 | A | 6/1983 | Berg | 556/440 |
| 4,392,828 | A | 7/1983 | Ehrnford | 433/217 |
| 4,407,984 | A | 10/1983 | Ratcliffe et al. | 523/115 |
| 4,490,115 | A | 12/1984 | Orlowski et al. | 433/199 |
| 4,503,169 | A | 3/1985 | Randklev | 523/117 |
| 4,514,174 | A | 4/1985 | Dougherty et al. | 433/226 |
| 4,514,342 | A | 4/1985 | Billington et al. | 260/952 |
| 4,544,359 | A | 10/1985 | Waknine | 523/115 |
| 4,547,531 | A | 10/1985 | Waknine | 523/116 |
| RE32,073 | E | 1/1986 | Randklev | 523/117 |
| RE32,299 | E | 12/1986 | Randklev | 501/59 |
| 4,636,533 | A | 1/1987 | Janda et al. | 522/14 |
| 4,640,936 | A | 2/1987 | Janda et al. | 522/14 |
| 4,649,165 | A | 3/1987 | Kuhlmann | 523/116 |
| 4,656,053 | A | 4/1987 | Angrick et al. | 427/53.1 |
| 4,658,558 | A | 4/1987 | Verble | 52/410 |
| 4,675,941 | A | 6/1987 | Grass | |
| 4,758,612 | A | 7/1988 | Wilson et al. | 524/5 |
| 4,814,362 | A | 3/1989 | Billington et al. | 523/117 |
| 4,816,495 | A | 3/1989 | Blackwell et al. | 522/14 |
| 5,009,597 | A | 4/1991 | Schaefer | 433/212.1 |
| 5,079,277 | A | 1/1992 | Wilson et al. | 523/116 |
| 5,089,051 | A | 2/1992 | Eppinger et al. | 106/35 |
| 5,106,304 | A | 4/1992 | Chronister | 483/228.1 |
| 5,228,907 | A | 7/1993 | Eppinger et al. | 106/35 |
| 5,252,697 | A | 10/1993 | Jacobs et al. | 528/60 |
| 5,338,773 | A | 8/1994 | Lu et al. | 523/116 |
| 5,350,782 | A | 9/1994 | Sasaki et al. | 523/116 |
| 5,354,785 | A | 10/1994 | Rheinberger et al. | 523/116 |
| 5,356,951 | A | 10/1994 | Yearn et al. | 523/115 |
| 5,378,737 | A | 1/1995 | Jacobs et al. | 523/116 |
| 5,418,262 | A | 5/1995 | Gobel | 523/116 |
| 5,425,640 | A | 6/1995 | Scharf | 433/215 |
| 5,538,129 | A | 7/1996 | Chester et al. | 206/63.5 |
| 5,547,379 | A | 8/1996 | Hasel | 433/212.1 |
| 5,548,001 | A | 8/1996 | Podszun et al. | 523/116 |
| 5,548,002 | A | 8/1996 | Schwabe et al. | 5823/118 |
| 5,609,675 | A | 3/1997 | Noritake et al. | 106/35 |
| 5,621,119 | A | 4/1997 | Podszun et al. | 549/229 |
| 5,645,429 | A | 7/1997 | Blackwell et al. | 433/217.1 |
| 5,707,440 | A | 1/1998 | Hengchang et al. | 106/485 |
| 5,710,194 | A | 1/1998 | Hammesfahr et al. | 523/116 |
| 5,846,075 | A | 12/1998 | Suh et al. | 523/115 |
| 5,944,527 | A | 8/1999 | Hasel | 433/21.1 |

FOREIGN PATENT DOCUMENTS

| | | |
|---|---|---|
| EP | 509516 | 10/1992 |
| EP | 530926 | 3/1993 |
| EP | 0368657 | 8/1993 |
| EP | 0434334 | 2/1994 |
| EP | 0159887 | 7/1994 |
| EP | 839511 | 6/1998 |
| WO | 92/08419 | 5/1992 |
| WO | 96/03090 | 2/1996 |

* cited by examiner

DENTAL COMPOSITE RESTORATIVE MATERIAL AND METHOD OF RESTORING A TOOTH

This is a divisional application of U.S. patent application Ser. No. 09/136,320 filed Jul. 6, 1998, now U.S. Pat. No. 6,353,040 which is a Continuation Application of Ser. No. 09/052,180 filed Mar. 31, 1998, and Ser. No. 08/946,612 filed Oct. 7, 1997, now both abandoned, which is a ordinary application claiming the benefit from Provisional Application No. 60/043,812 filed Apr. 14, 1997 and Provisional Application No. 60/042,585 filed Apr. 2, 1997.

TECHNICAL FIELD

The present invention relates to a dental composite material of the type useful in tooth restorations and the like, such as for example, as an alternative to a conventional dental amalgam or composite. More specifically, the invention relates to such a material having a hardenable matrix component and a filler component. Specifically, the invention relates to such a material wherein said filler component includes fillers having three different particle sizes. A method according to the invention includes compacting a dental composite material into a prepared tooth cavity, wherein the material has a packability index above about 300 g/mm².

BACKGROUND OF THE INVENTION

Certain practical considerations apply to the formulation and application of dental restorative, such as resin-based posterior dental restoratives. Accordingly, it is greatly preferred that the restorative composition be effectively homogeneous such that air bubbles or structural discontinuities are substantially avoided from introduction into the tooth structure. Additionally, it is preferred that such materials be "packable" or "condensable" and be capable of deforming a matrix band during the course of tooth filling. Such materials should also be capable of withstanding the physical stresses extant in the posterior region of the mouth and not crumble, fracture or erode under such conditions.

It has long been known to employ metallic amalgams in the restorations of posterior teeth. Such amalgam materials have been shown to have good resistance to the physical stresses experienced by posterior teeth and to posses small coefficients of thermal expansion. Such amalgams have also been demonstrated to have good "packability" and to demonstrate other properties necessary of the posterior restorative. Such materials however, suffer from uncertainty as to the biological effect of the introduction of mercury and other materials in the oral cavity over long periods of time.

Those skilled in the art of dental restoration will appreciate that certain posterior restorations, such as Class II restorations, require the employment of a matrix for proper application. This is to ensure that the replacement of the natural tooth structure is replaced and restored in close contact with the adjacent tooth. Thus, it will be appreciated that the use of a matrix band to surround the tooth to be repaired is generally necessary. Such bands are needed when the tooth to be repaired must be excavated in such a fashion that the resulting cavity preparation communicates from the top surface to one or more of the side surfaces of the tooth. In such a case, the matrix band is placed around the tooth and held tightly in place while a restorative material such as amalgam is put into place. A measure of a material's packability and values of the measured packability for conventional dental amalgams is described for example in U.S. Pat. No. 4,226,622 which is hereby incorporated by reference for such disclosure. Heretofore, conventionally and commercially available composite materials, while durable, have suffered from low packability values. This results in less than effective distention of the matrix band, often resulting in "rebound" or recovery of the band's original shape and ultimately to less than ideal contacts. A need exists therefore for a durable posterior dental composite material which has high packability.

THE OBJECTS OF THE INVENTION

It is an object of the present invention to provide a dental composite material.

It is another object of the present invention to provide a composite material as above, which is highly packable.

It is a further object of the present invention to provide such a composite material which is durable when used in dental restorations.

It is still another object of the invention to provide an alternative dental material to conventional amalgams and composites.

It is yet another object of the invention to provide a dental restorative material that can be placed where desired and then sculpted or carved for aesthetics.

These and other objects of the present invention which should become apparent from the description to follow, are carried out by the invention as hereinafter described and claimed.

SUMMARY OF THE INVENTION

In general, a dental composite material comprises a hardenable resin or compomer matrix and a filler component. The filler component comprises (a) a first plurality of glass particles having an average particle size of from about 1 to about 10 micrometers; (b) a second plurality of glass particles having an average particle size of from about 0.1 to about 1 micrometers; and, (c) a plurality of filler particles having an average particle size of from about 0.01 to about 0.04 micrometers. One embodiment of the invention comprises from about 12 to about 25 percent by weight of said resin matrix and from about 75 to about 88 percent by weight of said filler component.

A method according to the present invention for restoration of a tooth includes selecting a tooth in need of restoration, the tooth having an original conformation having at least a top surface and a side surface. A portion of the tooth is removed to form a cavity preparation. The cavity preparation may communicate from the top to surface to at least a first side surface of the tooth. At least the first side surface is surrounded with a matrix band substantially completely covering the cavity where it communicates with the first side surface. A dental composite material according to the invention, as discussed above and preferably having a packability index above about 300 g/mm², is applied to the cavity. The dental composite material is compacted to deform the matrix band, and the material is hardened, preferably by exposure to actinic light. The original conformation of the tooth is thereby substantially restored.

PREFERRED EMBODIMENTS FOR CARRYING OUT THE INVENTION

A dental composite or compomer material according to the present invention includes a hardenable resin and a filler component. The material can be put in place with respect to the dentition to be restored and then sculpted or carved as needed due to its non-flowing characteristics.

One preferred filler material is a radioopaque dental glass. More preferably, the filler component comprises at least one and preferably three components (a), (b) and (c) as follows: (a) a first plurality of preferably glass, more preferably barium glass, particles having an average particle size of from about 1 to about 10, more preferably from about 5 to about 9 micrometers; (b) a second plurality of preferably glass, more preferably barium glass, particles having an average particle size of from about 0.1 to about 1, more preferably from about 0.5 to about 0.9 micrometers; and, (c) a plurality of filler particles, preferably fumed silica, having an average particle size of from about 0.01 to about 0.04 micrometers. Filler (a) and (b) can be the same or different material. It has been found that this inventive material has improved packability greater than materials heretofore known in the art. The inventive materials can be used as an intraoral dental restorative, but can also be used by the laboratory technician in extra-oral dental applications such as in the production or restoration of crowns, inlays, and the like. The invention will be exemplified and discussed herein, for simplicity, with respect to intra-oral applications, it being understood that extra-oral applications are within the scope of the invention.

The material may be contained in a protective unit dose primary package, having an opaque polymeric cup thermosealed with a similar opaque polymeric or foil film lid. The inverted cup can be used to shield the light sensitive material during use. The material may also be packaged in a pouch or bag (not shown) having the characteristics of the package to be described below.

For example, a package embodying the concepts of the present invention is generally depicted by the number 10 on the attached drawings. As will be more fully discussed below, package 10 is useful for storing, transporting and using photosensitive materials such as material 11, which is the dental composite restorative material discussed herein.

Package 10 includes an open top container generally indicated by the number 20 having a base 21 and at least one upstanding wall 22 and having an open area 23 therein. (FIG. 4) Package 10 need be of no particular size or shape. It is preferred however, that package 10 be configured to closely hold a unit dose of material 11. One configuration of package 10 is generally rectangular, such that four sidewalls 22 contiguously formed with each other and with base 21 form container 20 (FIGS. 1, 3–5). Any other shape is within the scope of the invention, including having a singular round sidewall 22 as shown in FIG. 2 as package 10b.

An example of a unit dose of the present inventive composite material is about 0.3 grams. With such a unit dose, a package 10 having an open area 23 of about 300 mm$^2$ is useful. However, smaller or larger sizes are all within the scope of the invention.

Figures 1, 2, 3, 4:
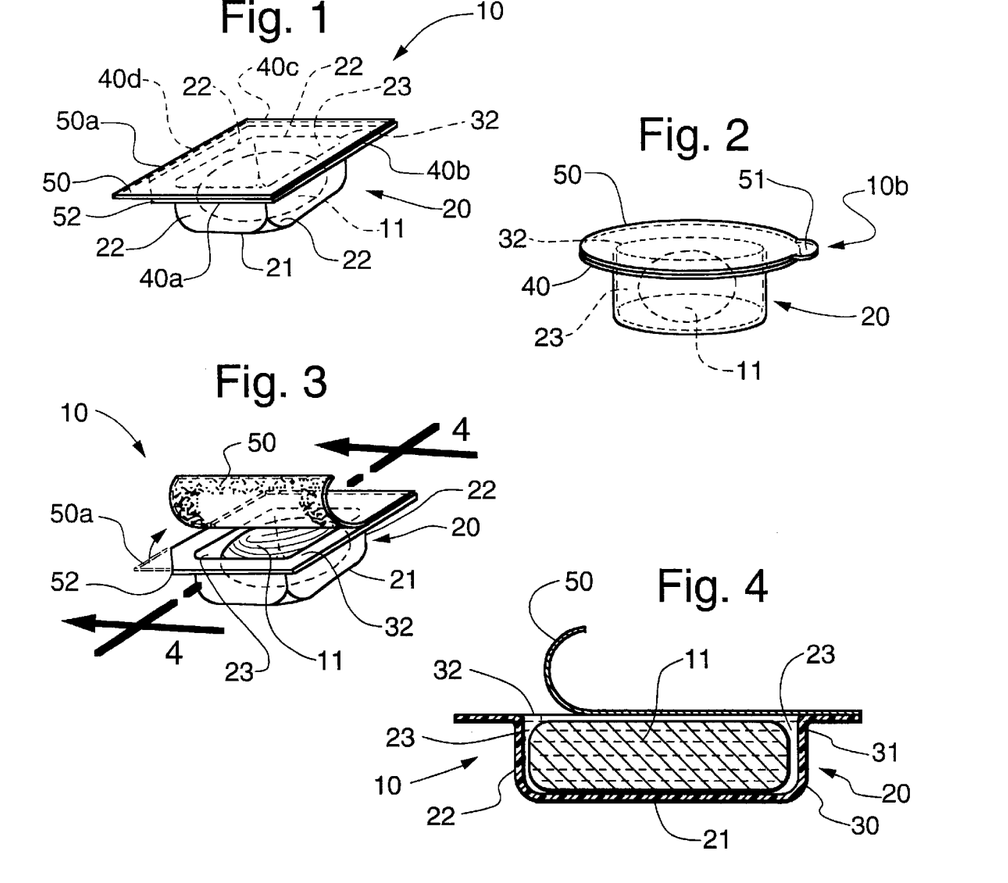
FIG. 1 is a perspective view of a package for photosensitive materials, according to the concepts of the present invention, and showing a unit dose of material contained therein by phantom lines.
FIG. 2 is a perspective view of an alternative embodiment of the package as shown in FIG. 1.
FIG. 3 is a view as in FIG. 1, showing the release layer partially removed therefrom, thereby exposing the unit dose of material contained therein.
FIG. 4 is a cross-sectional view taken along line 4—4 of FIG. 3.

Similarly, material 11 need not be of any particular shape, and may include flat or oblong shapes as shown in FIGS. 1 and 4, or more rounded shapes as shown in FIG. 2. The equipment (not shown) used to form the unit dose of material 11 or other criteria, will normally dictate the shape, and a configuration for package 10 may be selected based thereon. Shapes conducive to efficient material handling are envisioned, and all are within the scope of the invention. It is preferred that upstanding sidewall 22 be of sufficient height to allow a user to grasp sidewall 22 to effectively grasp package 10.

Sidewall 22 is preferably an upstanding wall having a first end 30 proximate to base 21 and an end 31 distal to base 21 (FIG. 4). Distal end 31 of sidewall 21 is proximate to an open top 32 which opens into open area 23.

Figure 5:
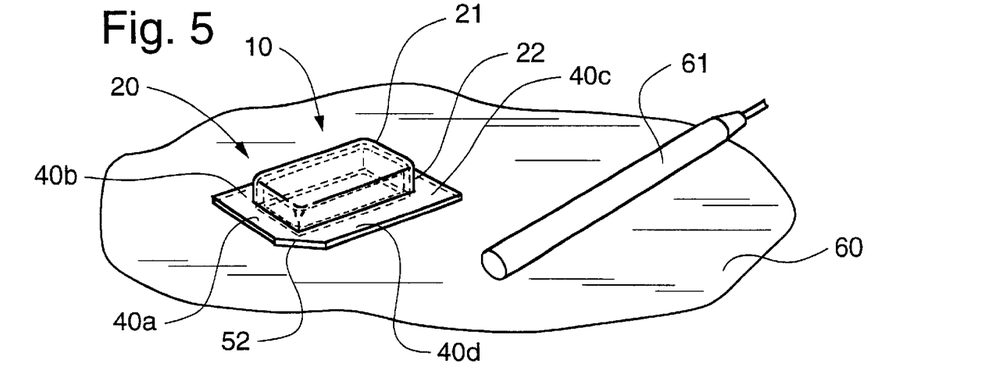
FIG. 5 is a perspective view of a portion of the package of FIG. 1, shown as being used on a support surface, and showing a dental instrument for environmental purposes.

Distal end 31 of sidewall 22 is preferably contiguously formed with a laterally extending shelf or web 40. In the characterization of the invention as depicted in FIGS. 1 and 5, web 40 has four portions 40a–40d. In the invention as shown in FIG. 2, a singular web 40 extends from sidewall 22.

Web 40 serves a number of functions, including providing a convenient surface for a user to grasp. Further, web 40 provides an extended surface for adhesive contact with a release layer to be described below. Web 40 also provides a connector between a plurality of contiguously formed packages 10 as depicted in FIGS. 6–9 and as will also be more fully discussed below.

A release layer 50 is removably and preferably adhesively affixed to web 40. Release layer 50 closes open area 23 by being placed in a proximate and opposing relation to open top 32. It is also preferred to configure release layer 50 to be of similar shape and dimension to web 40, although this is not necessarily required. Any releasable adhesive which will not detrimentally affect the unit dose of material 11 is useful. It will be further appreciated that release layer 50 may be selectively removed from package 10 and then replaced thereon to re-seal package 10.

Although an adhesively releasable release layer 50 is preferred, it is also within the scope of the invention to provide a release layer that is torn, cut or otherwise removed. All are within the scope of the term "release layer".

Figure 10:
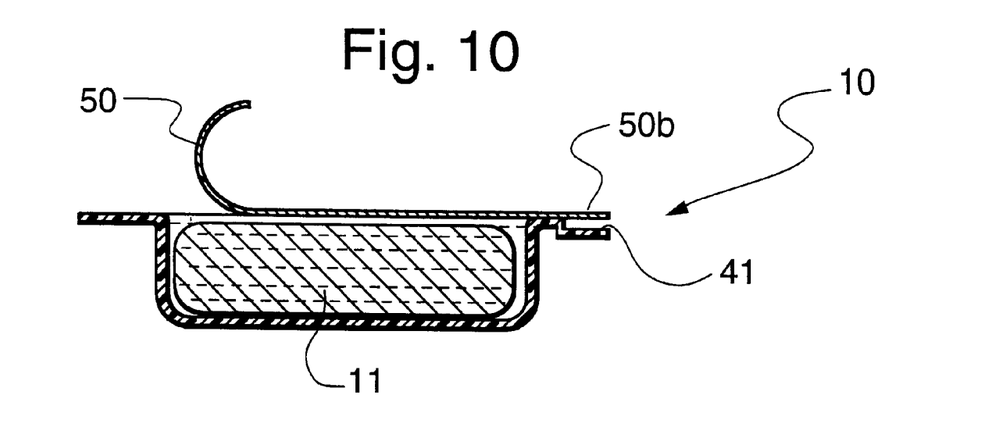
FIG. 10 is a cross-sectional view as in FIG. 4, showing an alternative embodiment of the invention.

To facilitate removal of release layer 50 from container 20, a user merely grasps a portion of release layer 50 and peels it from web 40 and distal end 31 of sidewall 22. To help the user in this procedure, a portion of release layer 50 may be left exposed. This may be accomplished by any means, such as by providing a tab 51 (FIG. 2) which does not contact web 40, or by removing (or forming without) a portion 52 of web 40 such that section 50a (FIG. 1) of release layer 50 is not in physical contact with web 40 at that location. Any such means or others are within the scope of the invention. As another example, as shown in FIG. 10, web 40 may terminate in a step lip or land 41 which also does not normally contact a proximate portion 50b of release layer 50. This provides an area where a user may grasp release layer 50 to remove it.

Package 10 is preferably substantially non-transmissive of at least a portion of the light spectrum to which the material 11 is photosensitive. It may be substantially non-transmissive of the entire light spectrum by being made of an opaque material, or it may be transmissive of all portions of the spectrum save that to which the material 11 is photosensitive. The latter is useful when it is desirable to be able to see the contents of package 10 for whatever reason.

Similarly, it is envisioned that a portion of package 10 may be opaque while another portion may be transmissive of all or part of the light spectrum. For example, container 20 may be made opaque while release layer 50 is made partially transmissive, or vice versa.

Package 10 is preferably thermoformed from black or dark pigmented plastic material providing a positive light barrier. Examples of such materials include polystyrene, polyethylene terephthalate, polyethylene (preferably high density polyethylene), polypropylene, and the like. Release layer 50 may be formed from a similar material or it may be formed from a flexible material such as a metallized substrate or a paper and foil (preferably aluminum) laminate, having a release coating or permanent sealable coating. With a permanent sealable coating, the package 10 may have to be destroyed, or a portion destroyed, to open. Release layer 50 and container 20 may also be individually formed from laminate materials. For reasons that will be explored below, release layer 50 may be flexible or rigid. FIGS. 3 and 4 depict a more flexible release layer 50 partially removed from package 20. A flexible release layer may be formed from a metallized substrate or a paper/foil laminate. A more rigid release layer 50 is depicted in FIG. 1 and may be formed from a more rigid or heavy plastic material. It will also be appreciated that package 10 may be formed with a lid attached by a living hinge, a sliding hinge, or any other useful lid, although these are not depicted in the drawings.

In use, a unit dose 11 of photosensitive material is provided in package 10. The unit dose of material 11 is protected from premature exposure to light because package 10 is substantially non-transmissive of at least that portion of the light spectrum to which material 11 is photosensitive. When it is desired to use material 11 for its intended purpose, the user will first remove release layer 50. At this point, the user may remove all or a portion of unit dose 11 from package 10. If a portion of material 11 is removed and a portion is left behind, then release layer 50 may be temporarily replaced onto container 20, thereby limiting continued exposure to light. This is further facilitated if release layer 50 is somewhat rigid.

Alternatively, the user may wish to remove all of unit dose of material 11 from package 10. In this instance, the material 11 may be placed on a support surface 60 (FIG. 5). A dental tool 61 used to work with material 11 is depicted in FIG. 5 for environmental purposes. To limit exposure of material 11 to light exposure in this instance, container 20 may be inverted over material 11 such that it covers material 11 as material 11 rests upon support surface 60.

In addition, release layer 50 may be placed upon support surface 60 and then material 11 placed upon the situated release layer 50 (not shown) before package 20 is placed over material 11. This provides an additional and convenient work surface for the user and again, may be facilitated by a relatively rigid release layer 40.

Figure 6:
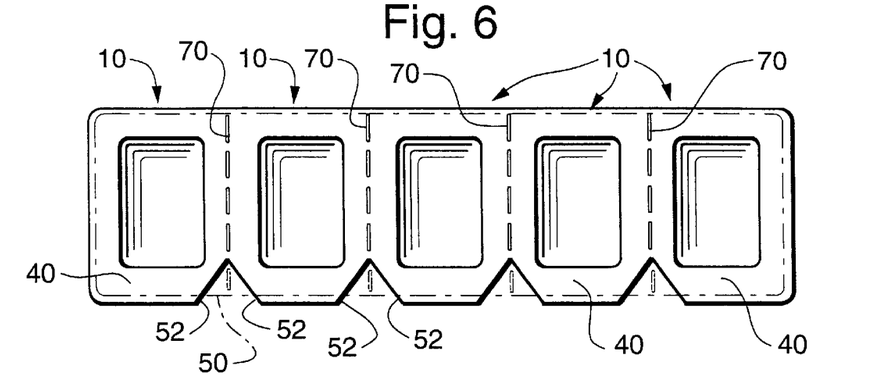
FIG. 6 is a top plan view of a plurality of packages as in FIG. 1, shown contiguously attached and showing a release layer in phantom lines.
Figure 7:
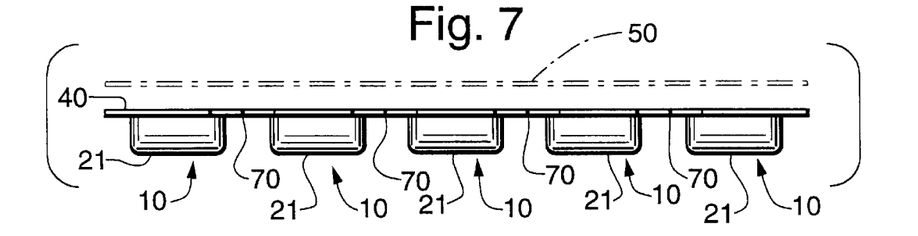
FIG. 7 is a side elevational view of the plurality of packages of FIG. 6, showing the release layer exploded therefrom.
Figure 8:
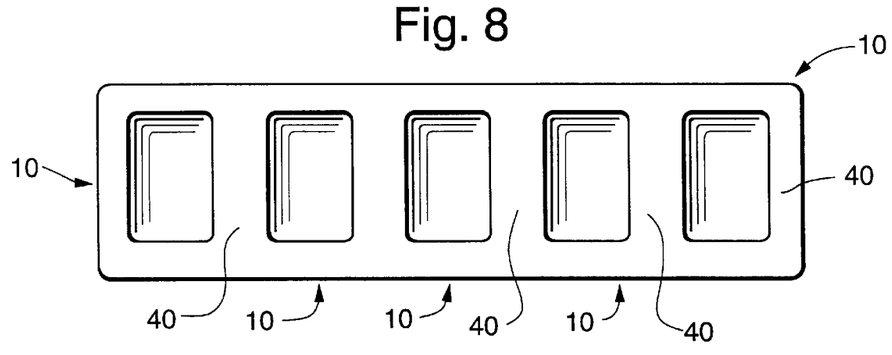
FIG. 8 is a top plan view of an alternative embodiment of the plurality of packages of FIG. 6.
Figure 9:
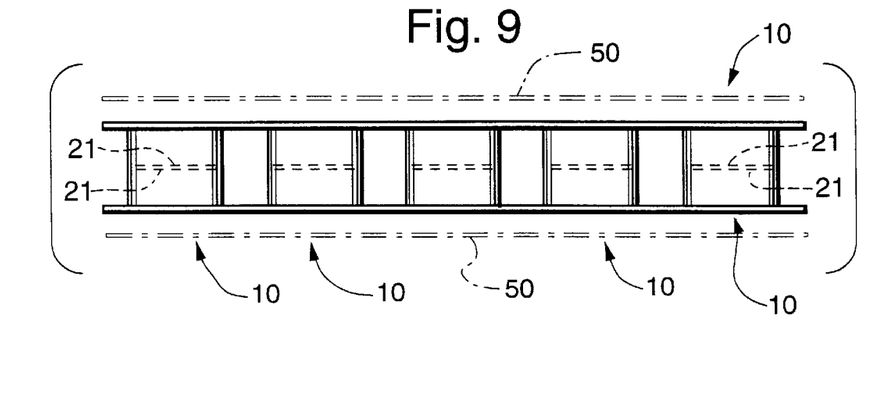
FIG. 9 is a side elevational view of two packages as in FIG. 7, shown as affixed back-to-back and each having a release layer shown in phantom lines and exploded therefrom.

Package 10 may be provided as an individual unit, as shown in FIGS. 1 and 2. However, package 10 may also be joined with one or more other packages 10 as shown in FIGS. 6–9. Any number of packages 10 so joined, and in any relationship are within the scope of the invention. For example, FIG. 6 depicts five packages 10 contiguously formed by being joined along a portion of web 40. Webs 40 between individual packages 10 may be provided with perforations 70, scored portions (not shown) or the like, to facilitate removal of one or more packages 10 from the others for use. Alternatively, as shown in FIG. 8, there need be no perforations and the joined packages 10 may be cut or torn from the others. No separation is necessarily required in use. Joining of a plurality of packages 10 need be accomplished by no particular means other than those conventional in the art.

Other configurations for joining a plurality of packages 10, such as joining bases 21 (FIG. 9) are also within the scope of the invention. Similarly, a plurality of packages 10 may be joined in rows and columns (not shown), or other configurations without limitation.

Returning now to a discussion of the inventive dental composite restorative material, the present materials are useful in many classes of tooth restorations, including but not limited to Class I, II and IV types and the like. In such restorations, the tooth to be restored is identified by the clinician and then excavated to remove decay or the like. It is a common practice in posterior tooth restorations, to employ a matrix band surrounding the tooth to be filled. These bands are generally thin, malleable metal or plastic sheets formed to fit over the tooth. Use of such bands and a general description of tooth restoration with which the present invention is useful, is described for example in U.S. Pat. No. 4,514,174 which is hereby incorporated by reference for such disclosures. By having improved packability over previously known dental composite materials, one skilled in the art will appreciate the improvement in tooth restorations that the inventive materials make possible. The composite materials according to the invention may be inserted into the cavity preparation by any conventional technique, including those described in U.S. Pat. No. 4,514,174 which is incorporated by reference. Those techniques similar to the handling and placement of dental amalgams, which techniques are well known in the art, are particularly useful with the present invention.

Examples of useful resins for compomers are those materials having as a principle functional ingredient, polymerizable unsaturated acidic monomers, such as a substituted butane moiety with acid or reactive acid derivative functionality. An example of an acid or reactive acid derivative functionality includes those having the general formula $(RO_2C)_x$—$C_4H_6$—$(CO_2R')_y$ where R is an acid radical or reactive acid derivative and R' is a polymerizable unsaturated radical having from about 2 to about 13 carbon atoms, x is 2 to 3 and y is 1 to 2. A description of such materials is provided in U.S. Pat. No. 5,218,070 which is hereby incorporated by reference for such disclosure.

Any hardenable resin matrix useful in intraoral or extraoral dental applications is within the scope of the invention. Preferred resins include those that are curable, more preferably curable by exposure to actinic light. Examples of such resins include ethoxylated bisphenol-A-dimethacrylate; Bisphenol-A-Glycidylmethacrylate; triethylene glycol dimethacrylate; and mixtures thereof. One preferred inventive material includes from about 12 to about 25 and more preferably from about 12 to about 18 percent by weight of the resin matrix component and from about 75 to about 88, more preferably from about 80 to about 88 percent by weight of the filler component. Optionally, a shading pigment or other additives may also be employed, such as for example, fluoride releasing agents, antibacterial agents, anticaries agents, and the like.

One preferred resin material is the reaction product of Bisphenol-A-Glycidylmethacrylate (Bis-GMA) and a chain initiator, such as hexamethylene diisocyanate (HMDI). The reaction may also include other reactive components. For example, the urethane component may be the reaction product of from about 27 to about 31 percent by weight of Bis-GMA as a reactive resin, more preferably about 29 percent by weight; from about 29 to about 33 percent by weight of triethylene glycol dimethacrylate (TEGDMA) as a reactive diluent, more preferably about 31 percent by weight; and, from about 29 to about 33 percent by weight of ethoxylated bisphenol-A-dimethacrylate (EBPADMA) also as a reactive diluent, more preferably about 31 percent by weight; with a useful amount of HMDI (preferably about 8 percent by weight). The reaction is preferably catalyzed with for example, a catalyst such as dibutyl tin dilaurate, and uses an inhibitor such as butylated hydroxy toluene.

From about 97 to about 99 percent by weight of the urethane component, and more preferably about 98 percent by weight, is used to form 100 percent by weight of the activated resin component. The remaining constituents of the activated resin include inhibitors, photoinitiators, UV absorbers, accelerators, fluorescing agents, and the like. While the preferred material is photocurable, a chemical cure package can also be used, including any of those well known in the art for dental use, including peroxide, amine, an ascorbic acid derivative, a metal ion salt, and the like.

Other useful resins can be employed including those disclosed in U.S. Pat. Nos. 4,514,342, 4,675,941, 4,816,495, 5,338,773 and 5,710,194 which are all hereby incorporated by reference for such disclosure.

The filler component preferably comprises one or more constituents, and more preferably comprises components (a), (b) and (c) as discussed above. It is believed that the mechanical interaction between these filler components, and particularly the increased contiguousness of contact therebetween, increases the packability of the inventive materials.

Examples of useful glass particles include barium aluminum-borosilicate glass, barium aluminofluorosilicate glass; mixtures thereof and the like. In these materials, barium can also be substituted by strontium and the like, and may also contain fluoride. Other useful materials include calcium hydroxy ceramics, and others such as those fillers disclosed in U.S. Pat. Nos. 5,338,773, 5,710,194, 4,758,612, 5,079,277, and 4,814,362, all of which are hereby incorporated by reference for such disclosure. These materials may have any morphology or shape, including spheres, regular or irregular shapes, filaments or whiskers, and the like. Any particle shape having the other characteristics of the invention as described herein, including for example, average particle size, is within the scope of the invention.

Preferred such glasses are also silanated although this is not an absolute limitation of the invention. The filler particles may be silane treated (silane coupled) or provided with other treatments as is conventional for dental fillers.

A preferred composition making up 100 percent by weight of the filler component, is comprises from about 10 to about 30, more preferably from about 12 to about 25 percent by weight, even more preferably about 15–20 percent by weight, of barium glass particles (a); from about 50 to about 65, more preferably from about 58 to about 62 percent by weight, even more preferably about 60 percent by weight of barium glass particles (b); and, from about 10 to about 30, more preferably from about 12 to about 25 percent by weight, even more preferably about 15–20 percent by weight, of fumed silica particles (c).

In addition to packability improvements, the materials according to the invention when compared to dental composite materials previously known, exhibit similar or improved physical characteristics. For example, these include depth of cure, diametral tensile strength, transverse rupture strength, flexural modulus, radioopacity, hardness, fracture toughness, opacity, polymerization shrinkage and wear. These characteristics and their comparisons with known compositions will be more fully explored hereinbelow. It has also been found that the present materials can be polished to a high luster with conventional polishing techniques. It will be shown that certain characteristics, especially packability and wear resistance are improved over the prior art materials.

Those skilled in the art will appreciate that "packability" as the term is used herein, is a quality possessed in relatively greater or lesser degrees between products including dental restoratives. It is difficult to attribute an exact quantitative measure to "packability" but a useful packability index has been devised. By "packability index" it is meant a measured value that describes the amount of force required, in grams per millimeter squared ($g/mm^2$), to condense or deform the restorative material. The test procedure simulates the clinical procedure of compressing the restorative material and packing the material into the cavity preparation to form a dense, substantially void-free mass. The higher the force required to compact the material the higher is the material's "packability index" and hence, the more "packable" the material. A material according to the present invention has a packability index of above about 300 and more preferably, above about 800 $g/mm^2$.

It has been found that compositions according to the invention have good or even improved aesthetic characteristics. The materials are polishable to a high lustre despite being highly filled. It has also been found that the products have excellent radiopacity approaching that of gold and amalgam products. It has further been found that the inventive materials have equal or superior post-cure or polymerization shrinkage characteristics as compared to conventional materials. This will be more full explored below.

A method according to the present invention for restoration of a tooth includes selecting a tooth in need of restoration, the tooth having an original conformation having at least a top surface and a side surface. A portion of the tooth is removed excavated to form a cavity preparation. The cavity preparation may communicate from the top surface to at least a first side surface of the tooth. In the case where a matrix band is required, at least the first side surface is surrounded with a matrix band substantially completely covering the cavity where it communicates with the first side surface. A dental composite material according to the invention, as discussed above and preferably having a packability index above about 300 $g/mm^2$, is applied to the cavity. The dental composite material is packed to deform the matrix band, and the material is hardened, preferably by exposure to actinic light. The original conformation of the tooth surface and anatomy, is thereby substantially restored.

General Experimental

In order to demonstrate the effectiveness of the inventive materials in carrying out the objects of the invention, a composite material was prepared containing the components as follows and as was discussed above:

| | Amount |
|---|---|
| Activated Resin: | 14.95 wt./wt. % |
| Inorganic Fillers: | 85.00 wt./wt. % |
| Shading Pigments: | 0.05 wt./wt. % |
| | 100.00 |

Activated Resin:

| | |
|---|---|
| Reactive Methacrylate Resin - EBPADMA Urethane Resin (Ethoxylated Bisphenol-A-Dimethacrylate); Inhibitor - BHT (Butylated Hydroxy Toluene); Photoinitiator - CQ (Camphorquinone); UV absorber - (Methanone Phenyl); Accelerator - EDAB (Ethyl, NN Dimethylamino Benzoate); and, | 98.0 wt./wt. % |
| Fluorescing Agent - 2,5 Dihydroxy Terepthalate Acid Diethyl Ester | 2.0 wt.wt. % |
| | 100.000 |

EBPADMA Urethane Resin:

| | |
|---|---|
| Reactive Resin - Bis-GMA (Bisphenol-A-Glycidylmethacrylate): | 28.9 wt./wt. % |
| Reactive Diluent - TEGDMA (Triethylene Glycol Dimethacrylate): | 31.3 wt./wt. % |
| Reactive Diluent - EBPADMA (Ethoxylated Bisphenol-A-Dimethacrylate): | 31.2 wt./wt. % |
| Chain Initiator - HMDI (Hexamethylene Diisocyanate): | 8.2 wt./wt % |
| Catalyst - Dibutyl Tin Dilaurate: | 0.3 wt./wt. % |
| Inhibitor - BHT (Butylated Hydroxy Toluene): | 0.1 wt./wt. % |
| | 100.0 |

Inorganic Filler Particles:

| | |
|---|---|
| (a) silanated barium aluminofluorosilicate glass (BAFG) | 20.0 wt./wt. % |
| (b) silanated BAFG | 60.0 wt./wt. % |
| (c) fumed silica | 20.0 wt./wt. % |
| | 100.0 |

As stated above, the present compositions are intended to be among other things, an alternative or replacement for conventional dental amalgams and composites. It has been found that the dental compositions according to this invention are equal to or superior to conventional dental amalgam products such as DISPERSALLOY available from Dentsply International Inc. of York, Pa. This includes for example, the wear characteristics of the material. To determine the wear properties of the inventive material, and standard wear test may be employed. Preferably the test is a three body wear test, which most closely approximates the mastication effects of teeth in normal use.

One such test uses the Leinfelder/University of Alabama in-vitro, three body cyclic abrasion wear machine. The Rank Taylor Hobson Profilometer/Surface analysis system, used in measuring material volume loss from the Leinfelder University of Alabama wear machine, performs two distinct functions: 1) The Form Taysurf profilometer employs a transversing stylus to construct a 3D topographic map of the worn area by means of an electronic interface unit linked to a host computer, 2) A surface analyzer program installed in the host computer graphically depicts the worn area and calculates its volume. This volume, expressed in cubic millimeters, is regarded as the "wear volume loss" of the material tested. The higher the volume loss, the greater the material wears. After a 400 k wear cycle run, a Dispersalloy (amalgam) test sample showed a wear volume of 0.024 $mm^3$; Alert (composite available from Jeneric/Pentron Incorporated) had a wear volume of 0.041 $mm^3$; Solitaire (composite from Kulzer) had 0.054 $mm^3$; and, Tetric Ceram (composite from Vivadent) had (at only 250 k wear cycles) 0.090 $mm^3$. In contrast, the material according to the present invention showed a volume loss of less than 0.024 $mm^3$. This data clearly shows an improved wear resistance (expressed in volume loss) for the material according to the invention in relation to both conventional amalgam and conventional composite dental materials.

The physical properties of this material, as such properties were discussed above, were tested by conventional techniques. As a comparison, the same physical properties were tested for Solitaire and Alert. The results of these tests are reported as follows:

| Property | Inventive Composite | Solitaire ® | Alert ™ |
|---|---|---|---|
| Depth of Cure @ 40" | 6.6 mm | 3.4 mm | 5.8 mm |
| Transverse Rupture Strength | 125 MPa | 75 MPa | 110 MPa |
| Flexural Modulus | 11,438 MPa | 3,964 MPa | 15,842 MPa |
| Radio-opacity | 2 mm Al | 2 mm Al | — |
| Barcol Hardness | 100 (med. scale) | 95 (med. scale) | 95 (med. scale) |
| Poly-merization Shrinkage | 2.29% | 3.50% | — |
| Packability Index | 844 $g/mm^2$ | 779 $g/mm^2$ | 465 $g/mm^2$ |
| Localized Wear Index | 0.022 $mm^3$ | 0.052 $mm^3$ | 0.029 $mm^3$ |
| Fracture Toughness | 1.65 $MPam^{1/2}$ | 1.34 $MPa^{1/2}$ | — |

Depth of cure is determined by preparing a small amount of the material to be tested by packing it into a cylindrical mold and radiating it with light by exposing the top surface of the cylinder to light. The specimen is then removed from the mold and the bottom surface of the sample is sanded to a predetermined hardness, such as a Barcol 7.0 on a medium scale. The thickness of the specimen is then measured. Other test parameters are tested according to conventional materials handling techniques. For example, diametral tensile strength was tested according to ADA 27; other properties were tested according to ISO 4049. Fracture toughness was tested according to Ruse et al., "Novel fracture toughness test using notchless triangular primsm (NTP) specimen", Journal of Biomedical Materials research, Vol. 31 (1996), pages 457–463, John Wiley & Sons, publisher.

The procedure used for determining the packability index may vary. By way of example, the procedure employed for the above reported packability index numbers employed an Instron Model 1123 Universal Testing Machine with Series IX Data Acquisition System. The sample holder included six cylindrical cups measuring 6.5 mm (millimeters) in diameter and 4.5 mm in depth (designed to simulate a tooth cavity). They were mounted in a solid block of plexiglass. The penetrator employed was a 3.15 mm diameter, 6.25 mm long, blunt tipped carbon steel pin vertically positioned in a proper Instron UTM fixture. The procedure employed was as follows:

A. Access Packability Test on the Instron computer and verify the following test parameters:

| | |
|---|---|
| Full Scale Loading: | 0.5 kg (kilograms) |
| Cross Head Speed: | 200 mm/minute |
| Extension Measurement: | 2.5 mm downward with automatic return |

B. Using a plastic spatula, fill each glass cup to its brim with the material to be tested. Gently fill the test material in the cup to prevent voids. Scrape away the excess material off the top of the cup so that the material surface is level with the cup brim. Allow the sample holder to achieve an ambient temperature of 23 C. (plus or minus 1) before testing, normally for at least one hour minimum.

C. Place the filled sample holder on the Instron load cell and calibrate to achieve a 0.00 kg load reading on the "Load" digital display window.

D. Center the first filled cup under the Penetrator and slowly lower the Instron cross head until the Penetrator just contacts the material surface (without penetrating it).

E. Set the extension measurement to read 0.00 mm on the digital "Extension" display window.

F. Press the appropriate computer key(s) to cause the cross head to lower (2.50 mm) and return.

G. Record the Packability Index value (as maximum grams/mm$^2$) by pressing the appropriate computer key(s).

H. Repeat the steps for the remaining five cups in the sample holder.

I. Press the appropriate computer key(s) to summarize and statistically analyze the test data.

The Packability Index is calculated by the following equation:

$$\text{Packability Index} = \frac{\text{Maximum Attained Force in Grams}}{\text{Area in mm}^2 \text{ of Penetrator Tip} (7.9 \text{ mm}^2)}$$

The Instron Series IX computer program automatically calculates the individual Packability Index values and prints the mean Packability Index expressing the value in grams/mm$^2$ (to a precision of 1 g/mm$^2$). Test results have no greater than a 10% coefficient of variation (CV). Specimen cups were cleaned with methanol between use.

Other examples of the inventive composition as exemplified above showed the following physical characteristics:

| Property/Characteristic | A | B | C | D |
|---|---|---|---|---|
| Packagbility Index - g/mm$^2$ | 872 | 794 | 844 | 847 |
| Polymerization Shrinkage - 0/0 | 2.50 | 2.45 | 2.29 | 2.35 |
| Localized Wear mm$^3$ | 0.0145 | 0.0221 | 0.0207 | 0.0236 |
| Flexural Strength - MPa | 132 | 120 | 125 | 139 |
| Flexural Modulus - MPa | 11,344 | 11,509 | 11,438 | 10,786 |
| Compression Strength - MPa | 322 | 332 | 320 | 325 |
| Diametral Strength - MPa | 45.3 | 46.3 | 46.5 | 51.0 |

-continued

| Property/Characteristic | A | B | C | D |
|---|---|---|---|---|
| Depth of Cure - mm | 6.3 | 6.6 | 6.6 | 506 |
| Barcol Hardness | 100 | 99 | 100 | 99 |
| Radiopacity - mm Al | 2 mm | 2 mm | 2 mm | 2 mm |
| Water Sorption - μg/mm$^3$ | 6.3 | 5.1 | 7.4 | 9.3 |
| Water Solubility - μg/mm$^3$ | 0.7 | 1.3 | 0.6 | 2.1 |

In another example of the inventive composition, a sample was prepared as above but with a filler component having 25 percent by weight of (a), 60 percent by weight of (b) and 15 percent by weight of (c). Tests were conducted as above and showed a compressive strength (MPa) of 302 (plus or minus 26); diametral tensile strength (Mpa) of 48 (±4); transverse strength (Mpa) of 127 (±12); a flexural modulus (Gpa) of 11 (±0.5); a wear volume loss (cubic mm at 400,000 cycles) of 0.0183; a packability (grams/square mm) of 765 (±42); a depth of cure (mm) of 7.3; and, a Barcol hardness on a medium scale of 99.

Still another test employing this filler component showed compressive strength (MPa) of 354; diametral tensile strength (Mpa) of 47; a flexural modulus (Mpa) of 11,814; a wear volume loss (cubic mm at 400,000 cycles) of 0.0167; a packability (grams/square mm) of 747; a depth of cure (mm) of 5.4; and, a Barcol hardness on a medium scale of above 100. This test sample also showed a post-cure shrinkage of 2.41 percent.

It is to be appreciated that the inventive material shows similar or improved physical characteristics compared to the commercially available product. Most notably, the inventive material shows an improved packability index and an improved localized wear index and the like.

The foregoing description illustrates preferred embodiments of the invention. However, concepts employed may, based upon the description, be employed in other embodiments without departing from the scope of the invention.

What is claimed is:

1. A method of working with a unit dose of photosensitive material comprising the steps of:

providing the unit dose of material in a package, wherein said material comprises a polymeric matrix and a filler component;

wherein said filler component comprises (a) a first plurality of particles having an average particle size of from about 1 to about 10 micrometers; (b) a second plurality of particles having an average particle size of from about 0.1 to about 1 micrometers; and, (c) a plurality of filler particles having an average particle size of from about 0.01 to about 0.04 micrometers;

said package having an open top container having a base and at least one upstanding wall and having an open area therein;

said at least one upstanding wall having a first end proximate to said base and an end proximate to said open top;

said end proximate to said open top being contiguously formed with a laterally extending web;

a release layer removably fixed to said web and enclosing said open area;

said container and said release layer being substantially non-transmissive of at least a portion of the light spectrum to which the materials are photosensitive;

removing said release layer from said package;

removing the unit dose of material from said package and placing the unit dose of material onto a support surface;

repeatedly removing a selected portion of the unit dose of material and inverting and placing said package over the unit dose of material; such that light is prevented from contacting the unit dose of material under said package.

2. A method as in claim 1, wherein said release layer is placed onto said support surface, and the unit dose of material is placed onto said placed release layer prior to said step of inverting and placing said package over the unit dose of material.

* * * * *